United States Patent [19]

Lim

[11] Patent Number: 4,690,682

[45] Date of Patent: Sep. 1, 1987

[54] SUSTAINED RELEASE

[75] Inventor: Franklin Lim, Richmond, Va.

[73] Assignee: Damon Biotech, Inc., Needham Heights, Mass.

[21] Appl. No.: 819,979

[22] Filed: Jan. 14, 1986

Related U.S. Application Data

[63] Continuation of Ser. No. 485,471, Apr. 15, 1983, abandoned.

[51] Int. Cl.⁴ .............................................. A61K 9/22
[52] U.S. Cl. .................................................. 604/891
[58] Field of Search ....................... 604/890, 891, 892; 424/19, 31, 34

[56] References Cited

U.S. PATENT DOCUMENTS

| | | | |
|---|---|---|---|
| 3,464,413 | 5/1967 | Goldfarb et al. | 604/306 |
| 3,474,777 | 10/1969 | Figge | 604/36 |
| 3,921,632 | 11/1975 | Bardani | 604/891 |
| 3,948,263 | 4/1976 | Drake, Jr. et al. | 604/891 |
| 3,993,072 | 11/1976 | Zaffaroni | 604/892 |
| 3,993,073 | 11/1976 | Laffaroni | 604/891 |
| 4,067,961 | 1/1978 | Laughlin | 604/890 |
| 4,324,683 | 3/1982 | Lim et al. | 252/316 |
| 4,352,883 | 10/1982 | Lim | 435/178 |
| 4,459,279 | 7/1984 | Stricker et al. | 424/19 |
| 4,475,916 | 10/1984 | Himmelstein | 604/890 |
| 4,478,596 | 10/1984 | Michelson | 604/890 |

FOREIGN PATENT DOCUMENTS

| | | |
|---|---|---|
| 52-3890 | 1/1977 | Japan . |
| 1414812 | 9/1972 | United Kingdom . |
| 1415210 | 6/1973 | United Kingdom . |

OTHER PUBLICATIONS

Leung et al., "Microencapsulation of Crystalline Insulin or Islets of Langerhans: An Insulin Diffusion Study", Artificial Organs, 7(2):208–212, Raven Press, New York, 1983.

"Science and Technology Brief", The Economist, Apr. 9, 1983, pp. 80–81.

Lim and Moss, "Microencapsulation of Living Cells and Tissues", J. Pharmaceutical Sci. 70(4):351–354, 1981.

Lim and Sun, "Microencapsulated Islets as Bioartificial Endocrine Pancreas", Science 210:908–910, 1980.

Primary Examiner—John D. Yasko
Attorney, Agent, or Firm—Lahive & Cockfield

[57] ABSTRACT

Disclosed are dispensing systems for releasing a substance at a substantially constant rate and methods for its manufacture. The composition comprises semipermeable capsules containing the material to be released. The capsules comprise membranes having pores of dimensions sufficient to control the kinetics of release provided there is maintained a large intracapsular concentration of the substance relative to the concentration desired in the extracapsular environment. The compositions may be produced by forming permeable capsules, suspending the capsules in a solution containing a high concentration of the substance to load the intracapsular volume, and then post-treating the capsules to reduce the size of the pores.

17 Claims, 5 Drawing Figures

SUSTAINED RELEASE

CROSS REFERENCE TO RELATED APPLICATION

This application is a continuation of Ser. No. 485,471 filed Apr. 15, 1983, now abandoned.

BACKGROUND OF THE INVENTION

This invention relates to microencapsulation. More particularly, it relates to a method of loading permeable microcapsules and a composition of matter comprising a permeable microcapsule containing one or more substances which may be released from the intracapsular volume at a substantially constant rate for a significant time.

Compositions of matter capable of sustained release of drugs, fertilizers, and the like are well known in the art. Generally, such compositions comprise a solid carrier in which the substance to be released is adsorbed or trapped as plural separate phases. When such compositions are placed in the environment in which they are intended for use, the outer layers of the solid carrier dissolve releasing a portion of the substance of interest. If the solid carrier dissolves slowly, then the substance of interest is released slowly or in discrete bursts over time. In use, the rate of release of the substance from such compositions necessarily is dependent upon the solubility of the carrier particle material, on the surface area of the carrier particle that at any given time is exposed to the environment, and often on the solubility of the substance in the environment of use. These factors typically result in a release rate which decreases over time.

In situations where it is desired, e.g., to release a drug at a constant rate into the circulatory system, the foregoing approach based on solubility properties cannot be used. In such situations, implantable mechanical perfusion pumps and similar devices have been suggested.

SUMMARY OF THE INVENTION

It has now been discovered that sustained release at a substantially constant rate can be achieved for essentially any substance by providing a solid or liquid reservoir of the substance within the interior volume of one or more capsules. Each of the capsules comprise a membrane having pores of dimensions sufficient to limit the rate at which molecules of the substance pass therethrough. The capsules are used in an environment which depletes the substance, e.g., by chemical modification, sorption, metabolic breakdown, ingestion, diffusion, or simple removal by fluid flow.

The concept of the invention involves loading permeable capsules with a reservoir of the substance of interest at a concentration sufficient to provide an osmotic pressure above a threshold level, and controlling the pore size of the capsule membranes so that passage of molecules of the substance through the membrane becomes the rate-limiting factor in dispensing the substance into the extracapsular environment. In one important embodiment, the substance of interest is a solid contained within the capsule together with a solvent for the solid. Once the solid and its solvent reach equilibrium, a reservoir of molecules of the solvent is available to provide a continuous, substantially constant migration of molecules through the membrane. In another embodiment, the substance is contained within the capsule as a solution at a concentration in excess of the desired extracapsular concentration. Molecules of the substance are released into the extracapsular environment at a substantially constant rate until the intracapsular concentration drops to a level where the intracapsular osmotic pressure is insufficient to support the membrane dependent transfer rate.

The intracapsular concentration of the substance to be dispensed should be quite high, typically at least two orders of magnitude greater than the desired extracapsular concentration, and more preferably at least three. Generally, the higher the intracapsular concentration the longer the constant release rate can be sustained. If the capsules are placed in an enviornment with no mechanism for removing the substance, then eventually the intracapsular and extracapsular concentration will equalize. Thus, capsules may be stored as a suspension in a volume of a compatible solvent containing a concentration of the substance substantially equal to or greater than the intracapsular concentration. In this circumstance net flow of the substance out of the capsules is prevented.

A preferred process for producing the dispensing systems of the invention involves forming capsules having membranes which permit traverse of the substance to be loaded therewithin, suspending the capsules in a concentrated solution of the substance one or more times to diffuse the substance into the intracapsular volume, and thereafter further treating the capsule to reduce the dimensions of the pores in the membrane.

A preferred method of making the capsules involves forming shape-retaining spheres, e.g., on the order of 0.1 mm to 3 mm in diameter from a water-soluble polymer containing plural anionic or cationic groups and cross-linking surface layers of the by contact with a polymer having plural groups of a charge opposite that of the water-soluble polymer. After loading, the capsule is again treated with the same or a different cross-linking polymer to reduce the dimensions of the pores.

One outstanding advantage of the process and dispensing system of the invention is that it can be modified readily to dispense essentially any substance desired at a controlled, substantially constant rate. Another advantage is that the capsule membranes can be fabricated from non-toxic materials that produce no significant immunological response, and accordingly are well suited for administration of biologically active materials such as hormones, antibodies, antigens, enzymes, lymphokines, vaccines, and natural or synthetic drugs via implantation in an animal body. Additional uses for the dispensing system of the invention include the sustained release of fertilizers, pesticides, fungicides, plant hormones and growth factors, flavors, perfumes, preservatives, and nutrients such as tissue culture nutrients.

In another aspect, the invention comprises a method of administering a substance to an animal comprising implanting, preferably by injection, one or more capsules of the type described containing the substance.

Accordingly, it is an object of the invention to provide a novel composition of matter capable of sustained release of a substance into an environment at a substantially constant rate. Another object is to provide a method of loading microcapsules. Another object is to release a biologically active material into an animal body at a substantially constant rate. Yet another object is to provide an improved method of controlling the pore size of a microcapsule membrane.

These and other objects and features of the invention will be apparent from the description which follows and from the drawing.

DESCRIPTION

Figure 1:
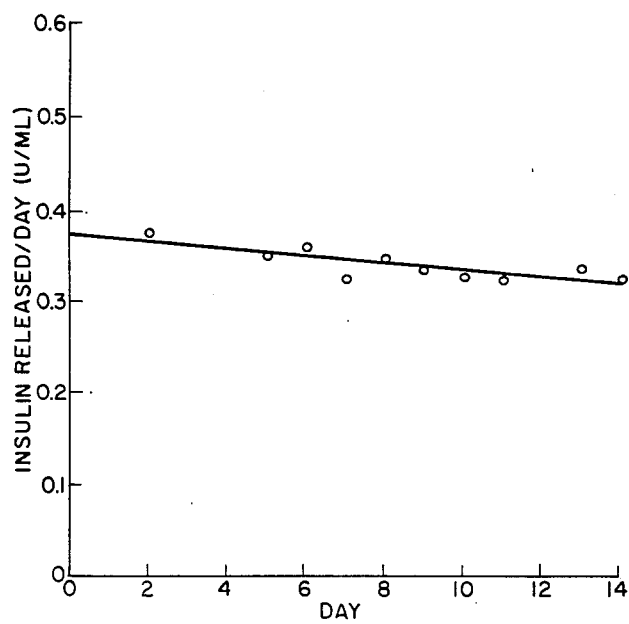
FIG. 1 is a graph of measured extracapsular insulin concentration versus time illustrating the substantially constant release rate of insulin using a composition embodying the invention which employs crystalline insulin.

The system of the invention involves the production of spheroidal capsules each of which comprise membranes having pores of dimensions small enough to hinder passage of molecules from a reservoir of a substance within the capsule. The rate at which molecules are released into the extracapsular volume is controlled by the kinetics of their passage through the membrane.

Well established principle of mass transfer across a porous membrane dictate that where the pores of the membrane are sufficiently large, and there is a concentration gradient across the membrane, solute will flow from the more concentrated region to the less concentrated region at a steadily falling rate until both sides of the membrane are in equilibrium. This equilibrium will also be attained where the pores of the membrane are of dimensions sufficient to hinder passage of mass across the membrane, provided some finite mass transfer occurs. However, in the latter situation, where the interior of a capsule membrane has a high concentration of the solute and the outside is at a low concentration, the passage across the membrane may be the diffusion rate limiting step. Accordingly, until such time that the concentration outside the capsule is high enough to produce a significant balancing osmotic pressure, or such time that the concentration of solute within the capsule becomes insufficient to generated sufficient osmotic pressure to drive the steady diffusion across the membrane, the rate at which solute molecules diffuse out of the capsule will be substantially constant.

The dispensing system of the invention is designed for use where some physical, chemical, or biological mechanism depletes the solute concentration immediately outside the capsule membranes. Accordingly, there is no significant buildup of the extracapsular concentration. Thus, for as long as there is a sufficient concentration of solute within the capsule, the diffusion kinetics are controlled by the capsule membrane. Once an equilibrium outflow of the solute is attained, diffusion proceeds at a substantially constant rate until the intracapsular concentration falls below a level where it influences the diffusion kinetics.

From the foregoing it is apparent that the ability to fabricate capsule membranes having the desired permeability characteristics, and the ability to load the capsules with a high concentration of the substance to be released are both important to the practice of the invention.

Procedures for encapsulation which enable some control of membrane porosity are known in the art, see, for example, U.S. Pat. No. 4,352,883. It has been discovered that by suitably modifying the procedures disclosed in the foregoing U.S. patent, the disclosure of which is incorporated herein by reference, it is possible to determine empirically a procedure for producing capsule membranes with the required permeability characteristics. The principles used to control membrane porosity are disclosed herein. Furthermore, several procedures for loading the capsules with a high concentration of the substance to be released have also been developed.

In the encapsulation technique of the '883 patent, a water-soluble polycationic or polyanionic polymer is formed into a spheroidal, shape-retaining droplet which suspends the material to be encapsulated. Thereafter, the droplet is exposed to a polymer having the opposite charge to cross-link surface layers of the droplet by the formation of salt bridges between the polyanionic and polycationic polymers. This procedure produces a porous membrane.

The material to be encapsulated is prepared in accordance with well-known techniques in finely divided or solution form, and a water-soluble polyanionic or polycationic material which can be reversibly gelled is added to the suspension or solution in low concentration. The droplet containing the material to be encapsulated is immediately rendered water-insoluble and gelled, at least in surface layers. Thereafter, the shape-retaining capsules are provided with a permanent semipermeable membrane. Where the material used to form the temporary capsules permits, the capsule interior may be reliquified after formation of the permanent membrane. This is done by reestablishing the conditions in the medium at which the material is soluble.

The material used to form the gelled droplets may be any water-soluble material which, by a change in the surrounding temperature, pH, or ionic environment or concentration, can be converted to a shape-retaining mass. The material must also comprise, for purposes of this invention, plural, easily ionized groups, e.g., carboxyl or amino groups which can react by salt formation with polymers containing plural groups which ionize to form species of the opposite charge. Preferred materials for forming the temporary capsule are water-soluble, natural or synthetic polysaccharides. Sodium alginate is most preferred. Other usable polysaccharides include carboxylated fractions of guar gum, gum arabic, charageenan, pectin, tragacanth gum, or xanthan gum.

These materials comprise glycoside-linked saccharide chains. Many contain free acid groups, which are often present in the alkali metal ion form, e.g., sodium form. If a multivalent ion such as calcium or strontium is exchanged for the alkali metal ion, the liquid, water-soluble polysaccharide molecules are "cross-linked" to form a water-insoluble, shape-retaining gel which can be resolubilized on removal of the ions by ion exchange or via a sequestering agent. While essentially any multivalent ion which can form a salt with the saccharides is operable, physiologically compatible ions, e.g., calcium, is preferred for purposes of making capsules designed for the sustained release of drugs. Other polysaccharides can be switched between the water-soluble and gelled, water-insoluble state simply by changing the pH of the medium in which they are dissolved.

In the next step of the process, a semipermeable membrane is deposited about the surface of the gelled droplets. The preferred technique for forming the membrane is to cross-link surface layers of the droplets by subjecting them to an aqueous solution of a polymer containing groups reactive with functionalities in the gel molecules. Certain long chain quaternary ammonium salts may be used for this purpose in some circumstances. When acidic gels are used, polymers containing acid reactive groups such as polyethylenimine, polyvinyl amine, and polypeptides such as polylysine may be used. In this situation, the polysaccharides are cross-linked by interaction between the carboxyl groups and the amine groups.

It has been discovered that permeability can be controlled sufficiently for purposes of the invention by selecting the molecular weight of the cross-linking polymer used, adjusting the concentration of the cross-linking polymer, and by cross-linking in two or more separate stages using the same or a different cross-linking agent. Generally, a solution of polymer having a low molecular weight, in a given time period, will penetrate further into the temporary capsules than will a high molecular weight polymer. In general, the higher the molecular weight and the less penetration, the larger the pore size. Broadly, polymers within the molecular weight range of 3,000 to 100,000 daltons or greater may be used, depending on the duration of the reaction, the concentration of the polymer solution, and the degree of permeability desired. The currently preferred molecular weight range is 20,000 to 80,000. Post-treating the capsule with the same or a different cross-linking polymer has the effect of reducing the dimensions of the pores and thickening the membrane.

At this point in the encapsulation, capsules may be collected which comprise a permanent semipermeable membrane surrounding a gelled solution of polysaccharide containing the core material. If mass transfer is to be promoted within the capsules and across the membranes, it is preferred to reliquify the gel to its water-soluble form. If low molecular weight polysaccharide is used, much of the excess material can be removed from within the membrane by diffusion. The liquification may be conducted by reestablishing the conditions under which the water-soluble polymer is a liquid, e.g., changing the pH of the medium or removing the calcium or other multifunctional cations. In the gels which are insoluble in the presence of multivalent cations, the medium in the capsule can be resolubilized simply by immersing the capsules in phosphate buffered saline, which contains alkali metal ions and hydrogen ions. Monovalent ions exchange with the calcium or other multifunctional ions when the capsules are immersed in the solution with stirring. Other salts, e.g., sodium citrate, may be used for the same purpose.

Lastly, depending on the type of semipermeable membrane formation technique employed, it is often desirable to treat the capsules so as to tie up free amino groups or the like which would otherwise impart to the capsules a tendency to clump. This can be done, for example, by immersing the capsules in a dilute solution of sodium alginate.

In this encapsulation technique it is difficult to synthesize the membranes while simultaneously retaining a high concentration of the substance to be encapsulated within the forming membrane unless the substance has a high molecular weight i.e., $\geq 300,000$. One solution to this problem is to encapsulate a solid material. After the capsules are completed, they are placed in the environment of use where solvent dissolves the intracapsular solid. Thus, there is produced within the intracapsular volume a reservoir of solute, at a concentration related to the solubility product of the solid in the solvent. The reservoir is maintained until the solid dissolves.

Another loading technique involves forming permeable capsules which have no initial loading or relatively low loading and thereafter suspending the capsules in a concentrated solution of the substance to be encapsulated. Thus, the capsules are loaded from the outside. Thereafter, the capsules are again treated with a polymeric cross-linking agent of the type described above to reduce further the dimensions of the pores.

When employing this outside loading technique, it is preferred that the solution in which the capsules are suspended be as concentrated as possible; at least three orders of magnitude greater than the extracapsular concentration desired during use of the compositions, and preferably even higher. Especially where the substance to be loaded has a high viscosity or a low solubility, it is preferred to repeat the outside loading procedure one or more times. It is also preferred to produce the capsule membrane at the outset so as to provide pores of dimensions sufficient to retard the passage of the solute into the capsule. This lengthens the loading time, but also minimizes leakage of the loaded materials during the time the second cross-linking step is being conducted to further reduce the pore dimensions and thicken the membrane.

From the foregoing it should be apparent that some experimentation will be required in the design of any specific composition for dispensing a given substance. However, in view of this disclosure those skilled in the art will be able to produce a variety of specific compositions having a desired constant rate of release. In some cases it is difficult to set the constant release rate of a given microcapsule at a specific desired level. However, it is relatively simple to control the average rate of release of a large number of capsules at an arbitrary value. Thus, dosage can be controlled by supplying a number of capsules which together release the desired quantity of the substance to be dispensed at a constant rate over a significant time.

Control of the permeability characteristics of the membrane is exercised by varying (1) the materials used to make the membranes, (2) the polymer concentration of the cross-linking solution, (3) the molecular weight of the cross-linking polymer or polymers, (4) the duration of the cross-linking step, and (5) the number of cross-linking steps conducted. While the effect on permeability characteristics of any one variable isolated from the others is difficult to define precisely, the following general comments can be made. Materials which have a high density of charged groups tend to result in highly cross-linked membranes characterized by smaller pore dimensions. Higher concentrations of polymer and longer exposures to the polymer tend to reduce the dimensions of the pores in the dimensions of the plane of the membrane, and produce thicker membranes with greater pore lengths. Low molecular weight materials tend to penetrate further into the gel. This typically results in reducing the permeability of the membrane. Cross-linkers having a molecular weight below about 3,000 daltons tend to permeate and react with substantially the entire gel sphere. Higher molecular weight materials form a relatively thin membrane on surface layers of the gel. Residual polysaccharide is available to bond with additional quantities of the cross-linker in multiple step cross-linking processes. The use of such multiple separate cross-linking steps tends to reduce the pore size.

The membrane is believed to comprise a matrix of polymers cross-linked with ionic bonds. The polymers define random intermolecular spaces which communicate with each other to form tortuous path pores through the membrane. It is also believed that both the pore dimensions and the effective length of the pore across the membrane influence the kinetics of molecular diffusion. Molecules in the volume of the pores presumably undergo many random collisions which in the aggragate determine the average time it takes for a molecule of a given effective dimension to traverse the membrane.

The substances which may be encapsulated in accordance with the invention to produce compositions characterized by substantially constant rate, sustained release can vary widely. The only limiting factors appear to be that it is difficult to produce a membrane that will be the dominating factor in controlling the diffusion rate in the case of very low molecular weight materials, e.g., 200 daltons or below. Also, capsule membranes uniformly permeable to substances having a molecular weight greater than about $10^6$ daltons are difficult to synthesize.

The invention will be further understood from the following non-limiting examples, wherein all percentages are given in a weight/volume basis (g/ml).

EXAMPLE 1

Crystalline Insulin Capsules

Gelled spheres were formed from 1.2% sodium alginate (NaG) in 0.9% NaCl containing 20 mg/ml (500 units) crystalline insulin. The NaG-insulin suspension was well mixed and the gell spheres prepared immediately so that the insulin was uniformly distributed in the NaG. Liquid spheroidal drops of the suspension were then immersed in a 1.5% $CaCl_2/H_2O$ gelling solution. After formation, the gelled spheres were allowed to remain in the $CaCl_2$ colution for three minutes and then treated as described below. All treatment and wash solutions had a volume of ten times the volume of the original NaG solution.

1. Treat with 0.6% $CaCl_2$ in 0.45% NaCl for five minutes, maintaining the gelled spheres in suspension.
2. Treat with 0.3% $CaCl_2$ in 0.68% NaCl for five minutes, maintaining the gelled spheres in suspension.
3. Wash twice with saline.
4. Treat with 60,000 molecular weight poly-1-lysine (PLL) in saline (13 mg PLL hydrobromide/dl) for five minutes, maintaining the capsules in suspension to form a membrane.
5. Wash twice in saline.
6. Wash with CHES buffer (2% 2(N-cyclohexylamino) ethanesulfonic acid in 0.6% NaCl, pH 8.2) diluted 1:20 with 1.1% $CaCl_2$.
7. Wash twice with saline.
8. Treat with 0.11% polyvinylamine (PVA, Polysciences, molecular weight range 50,000–150,000) in saline, pH 7.0, for five minutes, maintaining the capsules in suspension.
9. Wash three times in saline.
10. Treat with 0.6% NaG for five minutes, maintaining the capsules in suspension.
11. Wash twice in saline.
12. Treat with 0.5% PVA in saline for five minutes maintaining the capsules in suspension.
13. Wash three times in saline.
14. Store capsules in saline or 2.5% albumin in saline to stabilize the insulin.

Figure 2:
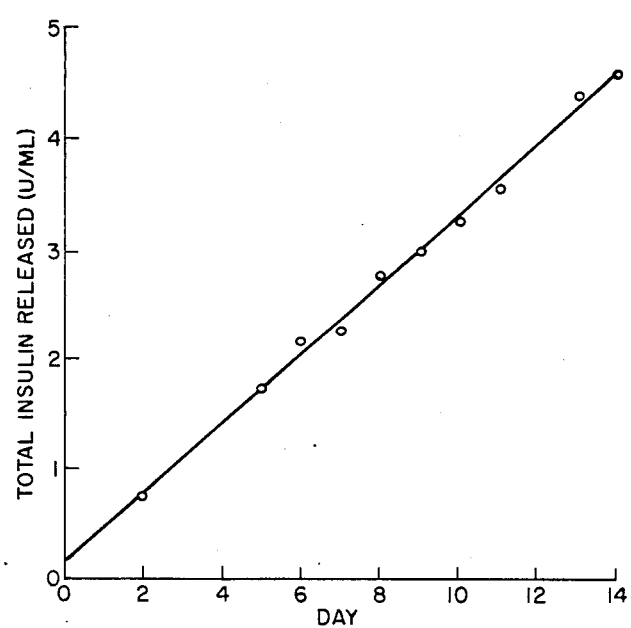
FIG. 2 is a graph of the cumulative extracapsular insulin concentration achieved using the preparation of FIG. 1.

The capsules were suspended in saline and the extracapsular concentration of insulin was assayed daily. As shown in FIG. 1, extracapsular concentration per day ranged uniformly between about 3 and 4 units of insulin/ml of extracapsular saline. As shown in FIG. 2, the cumulative insulin concentration in the extracapsular medium rises at a substantially constant rate.

EXAMPLE 2

Liquid Insulin Capsules

Blank gel spheres were made by dropping liquid spheres comprising 1.2% NaG in 0.9% saline into a 2.0% $CaCl_{12}/H_2O$ gelling solution. The $CaCl_2$ solution has a volume of 25 times that of the NaG solution. After formation, the gelled spheres were left in the $CaCl_2$ for three minutes then treated as described below. All treatments and wash solutions had a volume of ten times the volume of the original NaG solution.

1. Wash with CHES buffer diluted 1:20 with 1.1% $CaCl_2$.
2. Wash with 1.1% $CaCl_2$.
3. Treat with 60,000 molecular weight poly-1-lysine (PLL) in saline (6.7 mg PLL hydrobromide/dl) for four minutes, maintaining the capsules in suspension.
4. Wash with the CHES buffer-$CaCl_2$ solution as in step 1.
5. Treat with 0.11% polyvinylamine (PVA) in saline, pH 7.0,for four minutes, maintaining the capsules in suspension.
6. Wash three times with saline.
7. Treat with 0.6% NaG in saline for four minutes, maintaining the capsules in suspension.
8. Wash three times in saline.

This completes the formation of the blank microcapsules. These capsules may be stored in saline until ready for loading and further treatment of the membranes.

The capsules were loaded with insulin by suspending them in an equal volume of 500 units insulin/ml for 15 to 18 hours at 37° C. As much as possible of the extracapsular loading solution was then removed and the capsules were quickly washed once in four times their volume of saline. Immediately after washing the capsules were treated further using the procedure described below. All wash and treatment volumes were four times the volume of the capsules.

1. Treat the capsules with 0.33% PVA in saline, pH 7.0, for six minutes keeping the capsules in suspension.
2. Wash three times in saline.
3. Treat with 0.06% NaG in saline for four minutes.
4. Wash and store the capsules in saline.

Figure 3:
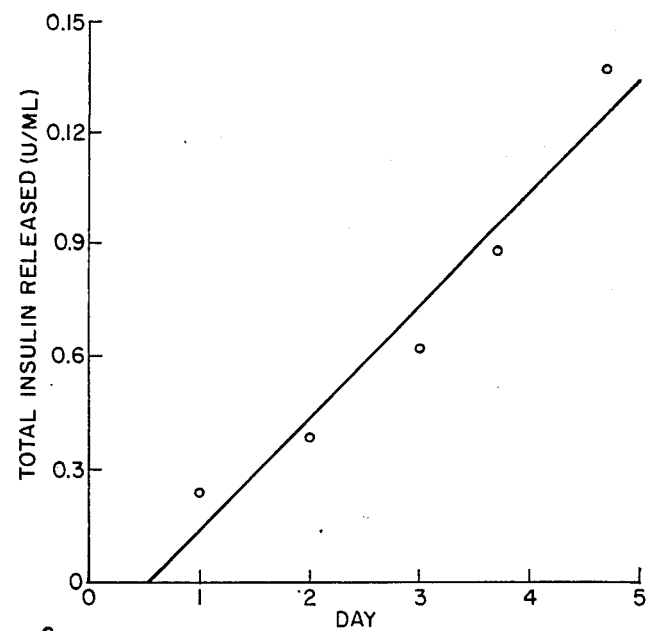
FIG. 3 is a graph of cumulative insulin concentration in an extracapsular medium versus time using a composition of the invention employing a solution of insulin.

The finished capsules were suspended in saline containing 2.5% albumin. Extracapsular insulin concentration was measured daily. The results are illustrated in FIG. 3. As shown, the cumulative insulin concentration increased at a substantially constant rate for a 5 day period.

EXAMPLE 3

Myoglobin Capsules

Blank gel spheres were made by dropwise addition of a 1.2% sodium alginate solution in saline, to a 1.5% $CaCl_2/H_2O$ gelling solution. The $CaCl_2$ solution had a volume of 25 times the volume of the NaG solution. After formation, the spheres were left in the CaCl$_2$ solution for four minutes and then treated as described below. All the solutions had a volume of ten times the volume of the original NaG solution.

1. Transfer to 0.6% CaCl$_2$ in 0.45% NaCl and allow to remain for five minutes.
2. Transfer to 0.3% CaCl$_2$ in 0.68% NaCl and allow to remain for five minutes.
3. Wash once in 0.9% saline.
4. Treat with 60,000 molecular weight poly-1-lysine (PLL) in saline (13.3 mg PLL hydrobromide/dl) for five minutes, maintaining the capsules in suspension.
5. Wash with saline three times.
6. Wash with CHES buffer diluted 1:20 with 1.1% CaCl$_2$/H$_2$O.
7. Treat with 0.17 polyvinylamine (PVA) in saline, pH 7.0, for five minutes, maintaining the capsules in suspension.
8. Wash three times with saline.
9. Treat with 0.06% NaG in saline for four minutes maintaining the capsules in suspension.
10. Wash two times in saline.
11. Treat with citrate solution (0.75% sodium citrate pH 7.4 in water).
12. Wash in 0.23% NaCl.

The blank capsules produced as disclosed above were loaded with myoglobin by suspending equal volumes of capsules and 2,000 mg/dl of myoglobin in saline for 15 to 18 hours. The capsules were then washed with saline until the supernatant was clear, and then further treated using the procedure described below. All treatment and wash volumes were four times the volume of the capsules.

1. Treat with 0.5% PVA in saline for five minutes maintaining the capsules in suspension.
2. Wash three times in saline.
3. Treat with 0.6% NaG in saline for four minutes maintaining the capsules in suspension.
4. Wash and store the capsules in 0.23% NaCl.

Figure 4:
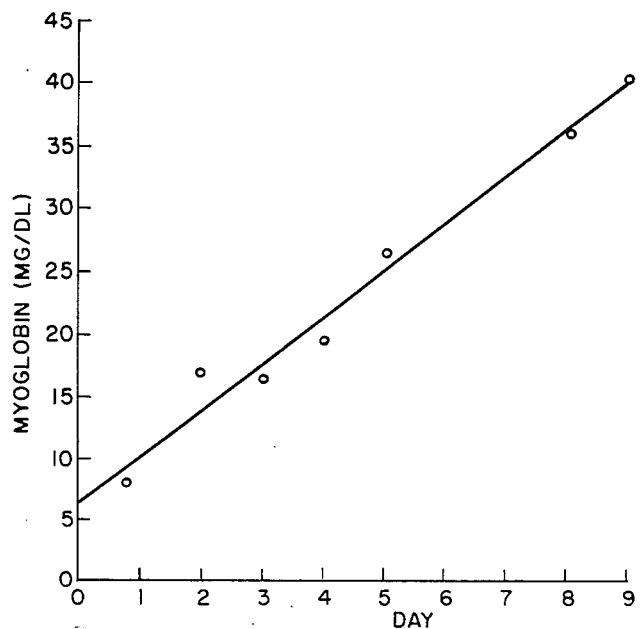
FIG. 4 is a graph of myoglobin concentration versus time illustrating the substantially constant rate of release of myoglobin.

The capsules were then suspended in saline and the extracapsular solution was periodically assayed for myoglobin content. The results are shown in FIG. 4. As illustrated, the cumulative myoglobin concentration increased at a substantially constant rate for nine days. These capsules released approximately 5–6 mg myoglobin per dl per day.

EXAMPLE 4

Hemoglobin Loaded Capsules

Blank gelled spheres were made by dropwise addition of a 0.9% sodium alginate (Sigma) solution in water to a 2% CaCl$_2$ aqueous gelling solution. The CaCl$_2$ solution had a volume of 25 times the volume of the NaG solution. After formation, the spheres were left in the CaCl$_2$ solution for five minutes and then treated as described below. All treatment and wash solutions had a volume of ten times the volume of the original NaG solution.

1. Wash with CHES buffer diluted with 1:20 with 1.1% CaCl$_2$.
2. Treat with 40,000 molecular weight poly-1-lysine in 0.9% NaCl (6.7 mg PLL hydrobromide/dl) for four minutes, maintaining the capsules in suspension.
3. Wash with the CHES buffer CaCl$_2$ as in step 1.
4. Wash three times in 0.9% saline.
5. Treat with 0.11% polyvinylamine (PVA) in saline pH 7.0 for four minutes, maintaining the capsules in suspension.
6. Wash three times in saline.
7. Treat with 0.06% NaG in saline for four minutes, maintaining the capsules in suspension.
8. Wash with saline three times.
9. Treat with 0.75% trisodium citrate in 0.7% NaCl pH 7.4 for six minutes.
10. Wash three times with saline.

The finished capsules are stored in saline until ready for loading and sealing.

The capsules were loaded with hemoglobin by suspending them in an equal volume of at least a 10% hemoglobin solution for 15 to 18 hours. To increase the internal hemoglobin concentration even higher, the hemoglobin solution was replaced and the above loading step was repeated. After loading, as much as possible of the loading solution was removed and the capsules were washed quickly in saline until the supernate was nearly clear (a small amount of hemoglobin will slowly leak out of the capsules at this stage). Immediately after this wash, the capsules are further treated using the procedures described below. All wash and treatment volumes were four times the volume of the capsules.

1. Treat the capsules with 0.17% PVA in saline, pH 7.0, for three minutes, maintaining the capsules in suspension.
2. Wash three times in saline.
3. Treat with 0.03% NaG in saline for four minutes.
4. Wash three times and store the capsules in saline.

Figure 5:
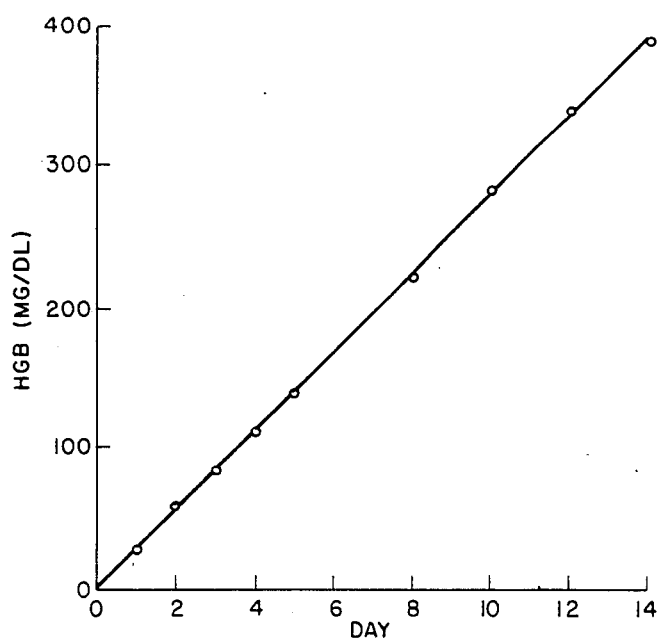
FIG. 5 is a graph of hemoglobin concentration versus time.

The hemoglobin capsules were suspended in saline and the extracapsular hemoglobin, concentration was assayed periodically. The results are set forth in FIG. 5. As shown, the capsules released approximately equal daily quantities of hemoglobin and over a 14 day period.

The foregoing exemplary systems demonstrate that in accordance with the processes disclosed herein it is possible to produce compositions of matter which release at a substantially constant rate substances in the low, medium, and moderately high molecular weight range. Insulin has a molecular weight on the order of $6 \times 10^3$, myoglobin has a molecular weight on the order of $1.8 \times 10^4$, and hemoglobin has a molecular weight on the order of $7 \times 10^4$.

Since, as disclosed above, the capsule membranes can be made with physiologically compatible, non-toxic materials such as polypeptides and polysaccharides, the capsules produce no significant detectable immunlogical response when injected into, e.g., a body cavity, under the skin, or into muscle tissue of an animal. Accordingly, various biologically active materials may be administered to animals at a substantially constant rate by implanting, preferably by injection, one or more capsules of the type described above. A substantially constant rate of release can be achieved for a significant period of time provided that the extracapsular concentration of the substance immediately adjacent the capsules does not build up to a level sufficient to alter the kinetics of release.

The compositions can be stored by suspending the capsules in a minimum volume of a solution of the substance contained in the intracapsular volume. Water-containing capsules may be suspended in a lipophilic vehicle to achieve the same purpose.

The invention may be embodied in other specific forms without departing from the spirit and scope thereof.

What is claimed is:

1. An injectable dispensing system for releasing a substance at a substantially constant rate in an environment immediately adjacent said dispensing system that depletes said substance, said system comprising:
   a microcapsule having a membrane comprising a matrix of polycationic polymer salt bonded to a polyanionic polymer which defines an intracapsular volume, said membrane having a multiplicity of pores of dimensions sufficient to limit the rate at which the molecules of said substance pass therethrough from said intracapsular volume; and
   disposed within said volume, for purposes of maintaining a given extracapsular concentration in said environment, a concentration of aid substance at least two orders of magnitude greater than said given extracapsular concentration which results in an osmotic pressure sufficient to sustain said limited rate when said capsule is placed in said environment.

2. The system of claim 1 wherein said substance is a solid disposed within said intracapsular volume in a solvent for said solid.

3. The system of claim 2 wherein said solid is sparingly soluble in said solvent.

4. The system of claim 1 wherein said substance comprises a biologically active material.

5. The system of claim 4 wherein said biologically active material is selected from the group consisting of hormones, enzymes, antibodies, vaccines, drugs, and lymphokines.

6. The system of claim 1 further comprising, for storage purposes, means defining an extracapsular volume of said substance adjacent the exterior of said capsule, said extracapsular volume containing a concentration of said substance sufficient to substantially prohibit a net flow of said substance from said intracapsular volume to said extracapsular volume.

7. The system of claim 1 wherein said membrane defines a sphere having a diameter between about 0.1 and 3.0 mm.

8. A process for administering a substance to an animal at a substantially constant rate for purposes of maintaining a given extracapsular concentration of said substance adjacent the exterior of said capsule within said animal, said process comprising the steps of:
   A. providing a dispensing system comprising:
      a microcapsule having a membrane comprising a matrix of polycationic polymer salt bonded to a polyanionic polymer which is physiologically compatible with said animal and which defines an intracapsular volume, said membrane having a multiplicity of pores of dimensions sufficient to limit the rate at which the molecules of said substance pass therethrough from said intracapsular volume; and
      disposed with said volume, a concentration of said substance at least two orders of magnitude greater than said given extracapsular concentration which results in an osmotic pressure sufficient to sustain said limited rate when said capsule is placed in said animal; and
   B. Injecting said dispensing system within the body of said animal.

9. The process of claim 8 wherein said dispensing system comprises a plurality of said capsules.

10. The process of claim 8 wherein said substance is a solid disposed within said intracapsular volume in a solvent for said solid.

11. The process of claim 10 wherein said solid is sparingly soluble in said solvent.

12. The process of claim 8 wherein said substance comprises a biologically active material.

13. The process of claim 12 wherein said biologically active material is selected from the group consisting of hormones, enzymes, antibodies, vaccines, drugs, and lymphokines.

14. A dispensing system for releasing a substance at a substantially constant rate in an environment immediately adjacent said dispensing system that depletes said substance, said substance comprising:
   a microcapsule having a membrane comprising a matrix of polycationic polymer salt bonded to a polyanionic polymer which defines an intracapsular volume, said membrane having a mulitplicity of pores of dimensions sufficient to limit the rate at which the molecules of said substance pass therethrough from said intracapsular volume; and
   disposed within said volume, for purposes of maintaining a given extracapsular concentration in said environment, a concentration of said substance at least two orders of magnitude greater than said given extracapsular concentration which results in an osmotic pressure sufficient to sustain said limited rate when said capsule is placed in said environment.

15. The system of claim 14 wherein said substance is selected from the group consisting of plant fertilizers, pesticides, fungicides, and plant hormones.

16. The system of claim 14 wherein said substance is selected from the group consisting of flavors, perfumes, and preservatives.

17. The system of claim 14 wherein said substance is a tissue culture nutrient.

* * * * *